United States Patent [19]

Engelhardt et al.

[11] Patent Number: 5,888,366
[45] Date of Patent: Mar. 30, 1999

[54] CAPILLARY MADE OF POLYMER MATERIAL HAVING A MODIFIED INSIDE SURFACE AND PROCESS FOR ITS PRODUCTION

[75] Inventors: Heinz Engelhardt, Saarbrucken; Thomas Schmitt, Tholey-Scheuern; Konstantin Shoiket, Sulzbach-Neuweiler, all of Germany

[73] Assignee: Hewlett-Packard Company, Palo Alto, Calif.

[21] Appl. No.: 914,124

[22] Filed: Aug. 19, 1997

Related U.S. Application Data

[63] Continuation of Ser. No. 612,607, Mar. 8, 1996, abandoned, which is a continuation of Ser. No. 315,324, Sep. 29, 1994, abandoned.

[30] Foreign Application Priority Data

Jan. 28, 1994 [EP] European Pat. Off. ............ 94101241

[51] Int. Cl.$^6$ .............. C25B 7/00; C25B 15/00; C25B 9/00; C25D 1/12
[52] U.S. Cl. .......... 204/471; 204/451; 204/452; 204/454; 204/601
[58] Field of Search .................. 204/450, 451, 204/452, 454, 601, 471

[56] References Cited

U.S. PATENT DOCUMENTS

| 5,114,768 | 5/1992 | Swedberg | 428/36.91 |
| 5,221,447 | 6/1993 | Hjerten | 204/601 |
| 5,228,969 | 7/1993 | Hernandez | 204/601 |
| 5,322,608 | 6/1994 | Karger et al. | 204/601 |
| 5,447,617 | 9/1995 | Shieh | 204/451 |

FOREIGN PATENT DOCUMENTS

395218  10/1990  European Pat. Off. .

*Primary Examiner*—Kathryn Gorgos
*Assistant Examiner*—Edna Wong

[57] ABSTRACT

A capillary made of plastics material that is suited for use in capillary electrophoresis. The capillary has its inner surface chemically modified for the generation of properties different from those of the original plastic capillary material. In the process of producing such capillaries, a premanufactured capillary is treated with a chemical reagent which generates functional groups directly on the capillary surface or generates attachment sites, on the capillary surface to which functional groups are later bonded.

24 Claims, 9 Drawing Sheets

CAPILLARY MADE OF POLYMER MATERIAL HAVING A MODIFIED INSIDE SURFACE AND PROCESS FOR ITS PRODUCTION

This application is a continuation of application Ser. No. 08/612,607 filed Mar. 8, 1996 now abandoned, which is a continuation of application Ser. No. 08/315,324 filed Sep. 29, 1994 now abandoned.

FIELD OF INVENTION

This invention relates to a capillary made of plastics material for use in capillary electrophoresis.

BACKGROUND ART

Capillary electrophoresis is widely applied in analytical and preparative separation processes in chemistry, biochemistry, and biotechnology. Conventional capillaries made of fused silica suffer from a number of drawbacks as they lack chemical stability. When subjected to high pH values, lack physical stability under mechanical stress, and during operation they show poorly reproducible electroosmotic flow (EOF) values after an exchange of the buffer solution. Developments to overcome these drawbacks have provided capillaries made of synthetic polymer materials such as polyethylene (PE), polypropylene (PP), poly(vinyl chloride) (PVC), polyfluorocarbon (PFC), and the like, for example. Studies of the electrokinetic properties of PE, PVC and PFC capillaries in aqueous solutions in dependence on pH are reported by Schutzner, W. and Kenndler, E. in: Anal. Chem. 64 (1992), p. 1991–1995. In the J. Microcolumn Separations, Vol. 5, No. 3, 1993, pages 246 and 247 it is described to coat the inner surface of hollow fibres of poly(butylene terephthalate) or polypropylene with polymers of acrylamide by graft polymerization The capillaries made of silica or synthetic polymer materials both present another problem in the phenomenon of electroendosmosis or electroosmotic flow which arises from an electrokinetic potential between the solid capillary wall and the liquid medium. A further problem with polymer capillaries is the adsorption of substrates to be separated by the capillary wall. These phenomena interfere with the mobility characteristics of the components involved and may deteriorate component separation efficiency and decrease resolution.

THE INVENTION

It is an object of the present invention to provide a capillary made of plastic material for use in capillary electrophoresis which overcomes the problems known with capillaries as used in the state of the art, which can be prepared from commercially available base capillary material by an easy procedure and in an inexpensive manner, which is reliable during application under a wide range of operational conditions, allows easy optical detection by means of common detectors, and has a long service life.

This object is achieved by a capillary made of plastic material for use in capillary electrophoresis with an inner surface of the plastic material being chemically modified for the generation of properties different from those of the original plastics capillary material. In particular, the capillary according to the invention has an inner surface of improved active properties, as compared to the original capillary material, in the form of created functional groups.

Suitable synthetic polymer materials for capillaries according to the invention are preferably non-conductive, thermoplastic polymers and copolymers, including polyethylene (PE), polypropylene (PP), polyamides (PA), polyvinyl alcohol (PVA), polyvinyl chloride (PVC), poly(butylene terephthalate) (PBT), and the like, in particular polyfluorocarbon (PFC), poly(tetrafluoroethylene) (PTFE), and poly (etheretherketone) (PEEK). In a preferred embodiment of the present invention the capillary is made of PEEK material. In another preferred embodiment the capillary is made of PTFE material.

The base capillary material can be provided in the form of commercially available synthetic polymer hollow fibres having a cross section of substantially cylindrical, or polygonal, or star shape, for example. In another embodiment of the present invention the capillary can be provided in the form of a plate made of synthetic polymer material with grooves introduced in an appropriate arrangement and a corresponding cover to form a closed capillary system. In a further embodiment the capillary can be provided in the form of a plastic component of accordingly adapted shape with a capillary system in the form of appropriate borings. The average inner diameters of the capillaries will usually be in the range of about 10 to 200 μm.

According to the present invention, the created functional groups can be at least one or more types of hydrophilic groups. In another embodiment the created functional groups can be one or more types of hydrophobic groups. Advantageously the functional groups are part of created individual functional residues. Also, the functional groups can substantially be formed of the base plastics material. Preferably the amount of functional groups present in the modified polymer capillary material is multifold increased over the amount of functional groups found in general in the untreated original capillary material. In particular the amount of functional groups is at least 10 times, preferably at least 100 times increased over the amount found with the untreated polymer capillary.

In the modified capillary according to the invention the functional groups can be chemically bonded to atoms of the base plastic material. The functional groups can be created from or are directly chemically bonded to sites of the base polymer capillary material. These additional functional groups have been created in addition to natural occurring active sites of the polymer. The functional groups may be indirectly chemically bonded to these sites of the base polymer capillary material, preferably by a spacer. Also, the functional groups can be both directly and indirectly bonded to the capillary material. Naturally, the types and numbers of bondings present may depend on the types and amounts of reagents used. Preferably, the functional residues are predominantly hydrophilic groups. In particular the functional groups can be hydroxyl groups. Also in particular, the functional groups can be amino groups or ammonium groups.

The created functional residues can be low-molecular components. In particular, individual created functional residues can have less than 10 functional groups, preferably less than 5 functional groups. Further in particular, individual created functional residues have less than 30 carbon atoms, preferably less than 15 carbon atoms.

On the other hand, the created functional residues can be high-molecular components. In particular high-molecular residues can be based on polyethylene polyamine with a molecular size of about 50000 Daltons or more.

With particular advantage the functional groups can be of a type and be present in an amount adapted to effect a desired variation in electrochemical behaviour. Preferably, the functional groups are adapted to control the electroosmotic flow (EOF). The type and number of functional groups created depends on the type and amount of modification in the EOF desired. A thus modified capillary according to the invention is particularly adapted for the separation of proteins. Further examples of the application of chemically modified capillaries of this invention in electrophoresis include chemical analysis in inorganic and organic chemistry, water analysis, environmental analysis, clinical analysis, monitoring and quality control of synthetic chemical, biochemical and biotechnological products, and drugs. The functional property of the inner surface of a capillary modified according to the invention can be such that proteins do at most only reversibly adhere, preferably they do not at all adhere thereon.

In the modified polymer capillary according to the invention, the functional groups can be non-ionic and/or ionic. The functional groups can be ionic with positive charge. Also, the functional groups can be ionic with negative charge.

Methods to create functional groups in the base polymer capillary material according to the present invention comprise any methods which alone or in combination are adapted to provide reactive sites or functional groups in or attached to the organic molecules of the surface of the plastics material. In particular, functional groups can be created in the capillary material by oxidation reactions. Also, functional groups can be created by reduction reactions. Further, functional groups can be created by elimination reactions. Carriers of functional groups and/or functional groups can be introduced to the capillary material by addition reactions. Also, they can be introduced by condensation reaction. Naturally, the type of reaction involved depends on the type of reactants used and can thus be selected according to the desired modification.

With capillaries made of nontransparent plastic material, an optical passage is provided to allow optical detection. In particular according to the invention, an optical passage is provided by sealingly inserting an optically permeable member. In one embodiment of the present invention, a wall section of the capillary is substituted by optically permeable material. Preferably, an optically permeable capillary section, preferably made of plastic material, can sealingly be inserted. Advantageously such a detection capillary section has a length of about 1 cm, a minimum inner diameter larger than or equal to the inner diameter of the plastic capillary, and a maximum inner diameter smaller than or equal to the outer diameter of the plastic capillary. In another preferred embodiment of the present invention, there can be at least two optical windows on opposite sides of the capillary, whereby in particular at least one optical lens be inserted. Optionally, two or more detection windows can be provided in the capillary at appropriate locations. Any capillary materials which are permeable to the radiation used for detection, in particular to UV radiation, can be applied as detection window materials. Preferably, the detection window can be inserted in the capillary after completion of the capillary surface modification. The above described optical passage to allow optical detection with capillaries made of nontransparent materials can be provided with any capillary material, preferably made of plastic material, be it modified according to the present invention, or modified according to any other method known in the art, or unmodified.

A process for the production of a capillary made of plastic material for use in capillary electrophoresis, includes at least treating a premanufactured capillary with a chemical reagent which generates functional groups directly on the capillary surface or generates attachment sites to which functional groups or carriers of functional groups can be bonded.

Preferably, according to the invention, active sites can be created on base polymer material chains. The active sites thus created can serve as functional groups to form a modified capillary material. In another embodiment of the present invention, the creation of active sites is a pretreatment step, with the thus created sites serving as attachment points for functional groups. The amount of reactive sites created substantially exceeds the amount of reactive sites in the untreated polymer capillary material. Preferably, the number of functional reactive sites is multifold increased over the amount of functional groups found in the untreated capillary material, preferably it is at least 10 times, most preferably at least 100 times increased over the amount found in the untreated polymer capillary. As compared to silica capillaries which have an amount of functional groups, e. g. OH groups, corresponding to about 3.5 $\mu M/m2$, the amount of functional groups present in a capillary modified according to the invention is considerably lower, in particular in the range of $1/10$ to $1/100$, i. e. $3.5 \times 10-1$ $\mu M/m2$ to $3.5 \times 10-2$ $\mu M/m2$, even after activation treatment.

Pretreatment methods for chemical activation of capillaries made of polymer material according to the present invention comprise redox reactions, preferably oxidation reactions using strong oxidants or reduction reactions using strong reductive agents. Appropriate reagents for the aforementioned redox reactions are usually known as corrosive media including chlorate, sulphuric acid, metal hydrides, metal organic compounds, for example. Also, pretreatment methods for modifying capillaries made of polymer material comprise elimination reactions. Appropriate elimination reagants include metal organic compounds. These pretreatments usually have an erosive action on the base polymer capillary material.

The chemically activated polymer material can be modified by subjecting it to at least one or more subsequent reaction steps. In one embodiment of the process according to the present invention, preformed carriers of functional groups can be introduced to the base polymer capillary material. In another embodiment, residues can be generated directly from the base plastic material on the capillary surface. Advantageously, carriers of functional groups are chemically bonded to polymer chains in the capillary surface. Also, the carriers of functional groups or the functional groups themselves can be chemically bonded via a spacer to polymer chains in the capillary surface. Further in the process according to the invention, the carriers can be chemically bonded via a linking member to polymer chains in the capillary surface, wherein preferably the linking member is introduced first and subsequently the functional group is bonded thereon. Advantageously, the linking member can act as a spacer.

Examples of further modification steps with PEEK capillaries subsequent to oxidative activation comprise further activation using carbonyl diimidazole or carbodiimide followed by reaction with an amine or polyamine to yield a PEEK amine derivative, or amination using a polyamine to yield a PEEK amine derivative which results to an inversion of the EOF behavior. Another modification step for PEEK pretrated by oxidation is esterification using chitosan, which results in an elimination of the EOF effect. Examples of further modification steps with PTFE capillaries subsequent to a fluorine elimination pretreatment step comprise hydroboration using boran in tetrahydrofuran to yield OH functional groups, or bromation followed by amination to yield $NH_2$ functional groups, or reaction with maleic acid anhydride to form reactive COOH groups followed by reaction with carbonyl diimidazole to yield carbodiimide functional groups, or oxidation using oxygen or $H_2SO_4$ and $KClO_3$ to yield oxidized PTFE, or reaction using acrylamide to yield polyacrylamide functional groups.

The above and still further objects, features and advantages of the present invention will become apparent upon consideration of the following detailed descriptions of several specific embodiments therof, especially when taken in conjunction with the accompanying drawings.

DESCRIPTION OF PREFERRED EMBODIMENTS

Figure 8:
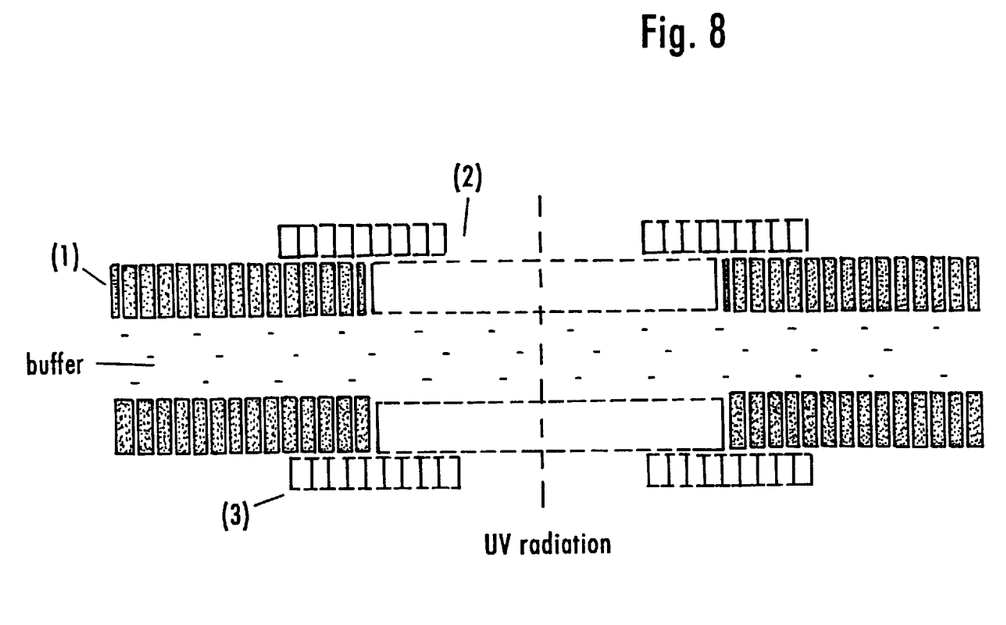
FIG. 8 is a schematic illustration of a detection capillary showing the connecting portion of two capillaries unpermeable to UV radiation.

The detection capillary shown in FIG. 8 is made of PEEK capillary material (1) which is impermeable to UV radiation. The base capillary is cut and a section made of silica (2) which is permeable to UV radiation inserted. Pieces of capillary made of plastic material (3) are provided as sealing connecting parts. The connecting portion does not exhibit a dead space.

Figure 9:
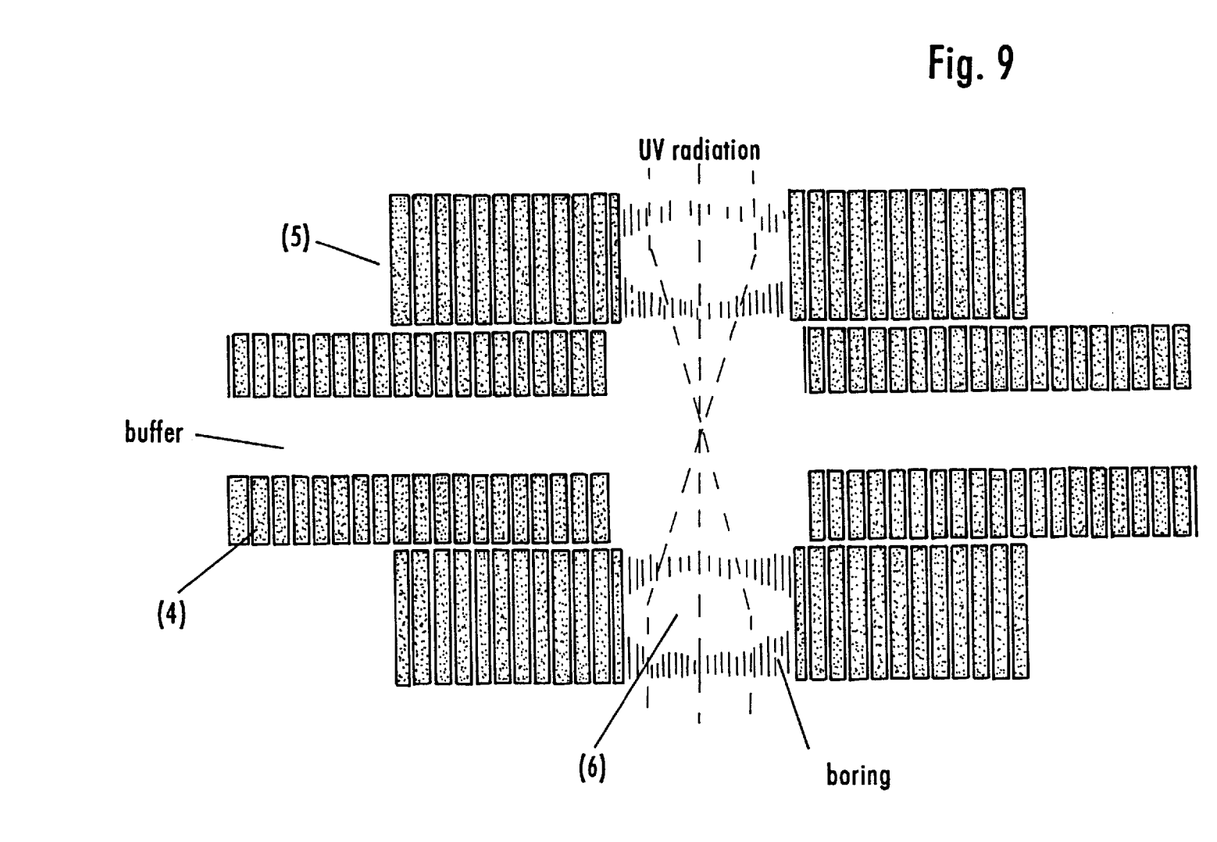
FIG. 9 is a schematic illustration of a detection capillary including spherical lenses.

The detection capillary shown in FIG. 9 is comprised of a nontransparent plastic capillary (4) which is cut off, an outer plastic capillary (5) with borings which each include a focusing spherical lens (6). The outer plastic capillary is sealingly arranged and has a relatively thicker wall. The boring is provided in transvers direction to the capillary axis, and in each of the openings is inserted a spherical lens to focus radiation in the capillary axis.

The present invention is further described in more detail by the following examples of preferred embodiments which are, however, in no way intended as limitations.

EXAMPLE 1

Figure 1:
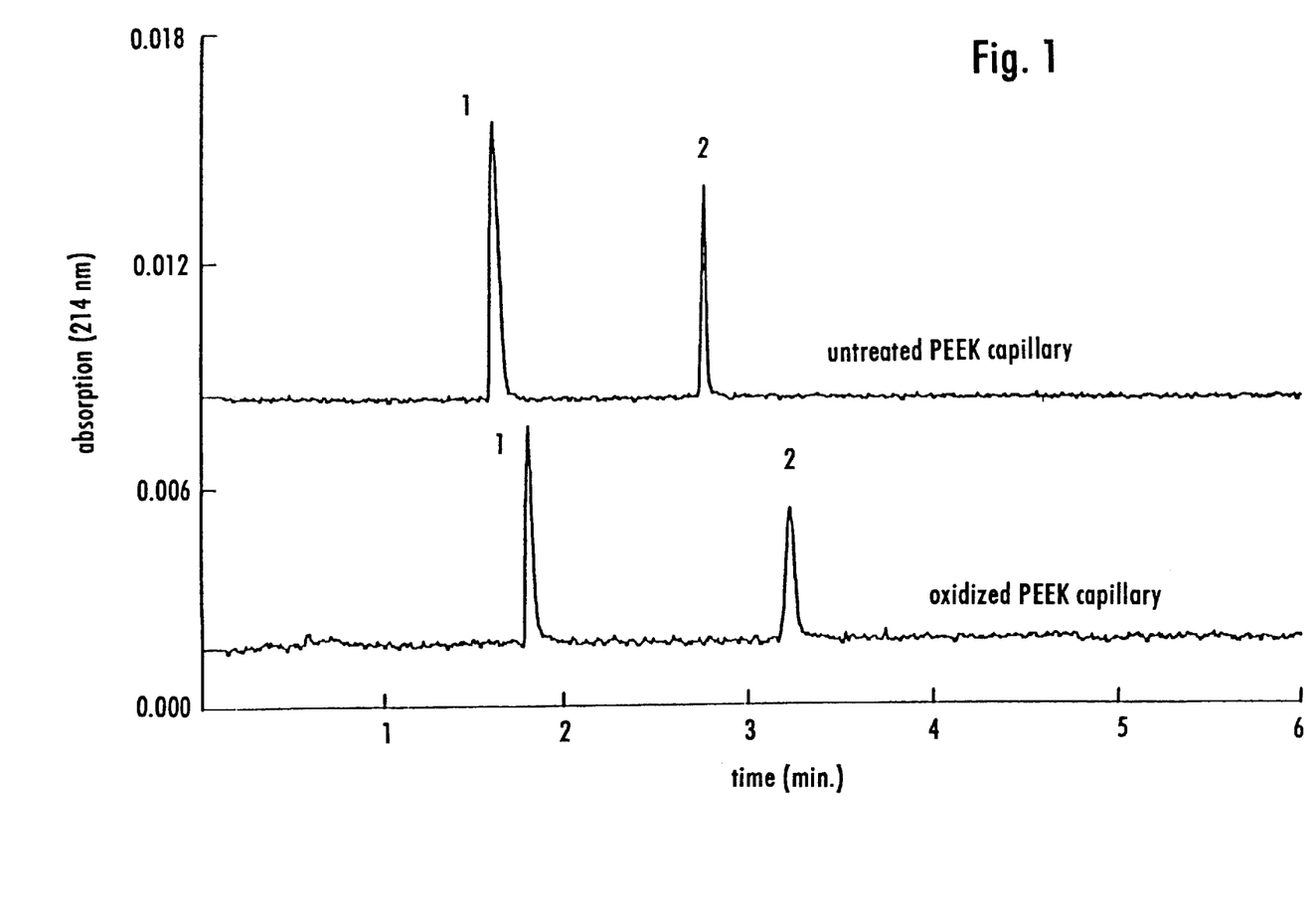
FIG. 1 is a comparison of an untreated and an oxidized PEEK capillary under separation conditions of L=20/27, E=540 V/cm, 10 mM phosphate buffer pH 7, trimethylphenylammonium bromide (1), benzyl alcohol (2).
Figure 2:
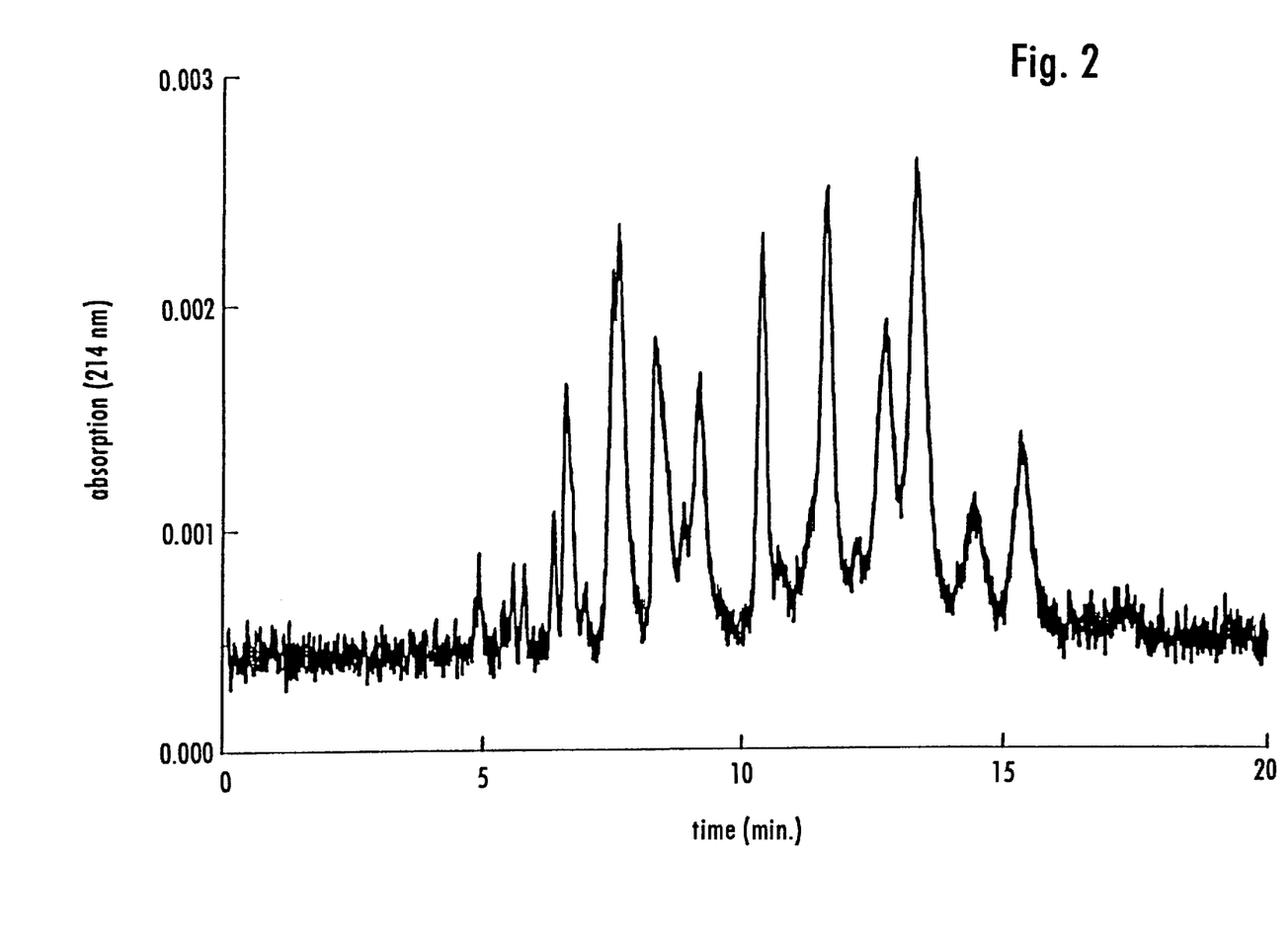
FIG. 2 is an electropherogram of an autolysate of trypsin in an oxidized PEEK capillary under separation conditions of L=29/35.5 cm, 50 gm ID, 10 mM phosphate buffer pH 3.0.
Figure 3:
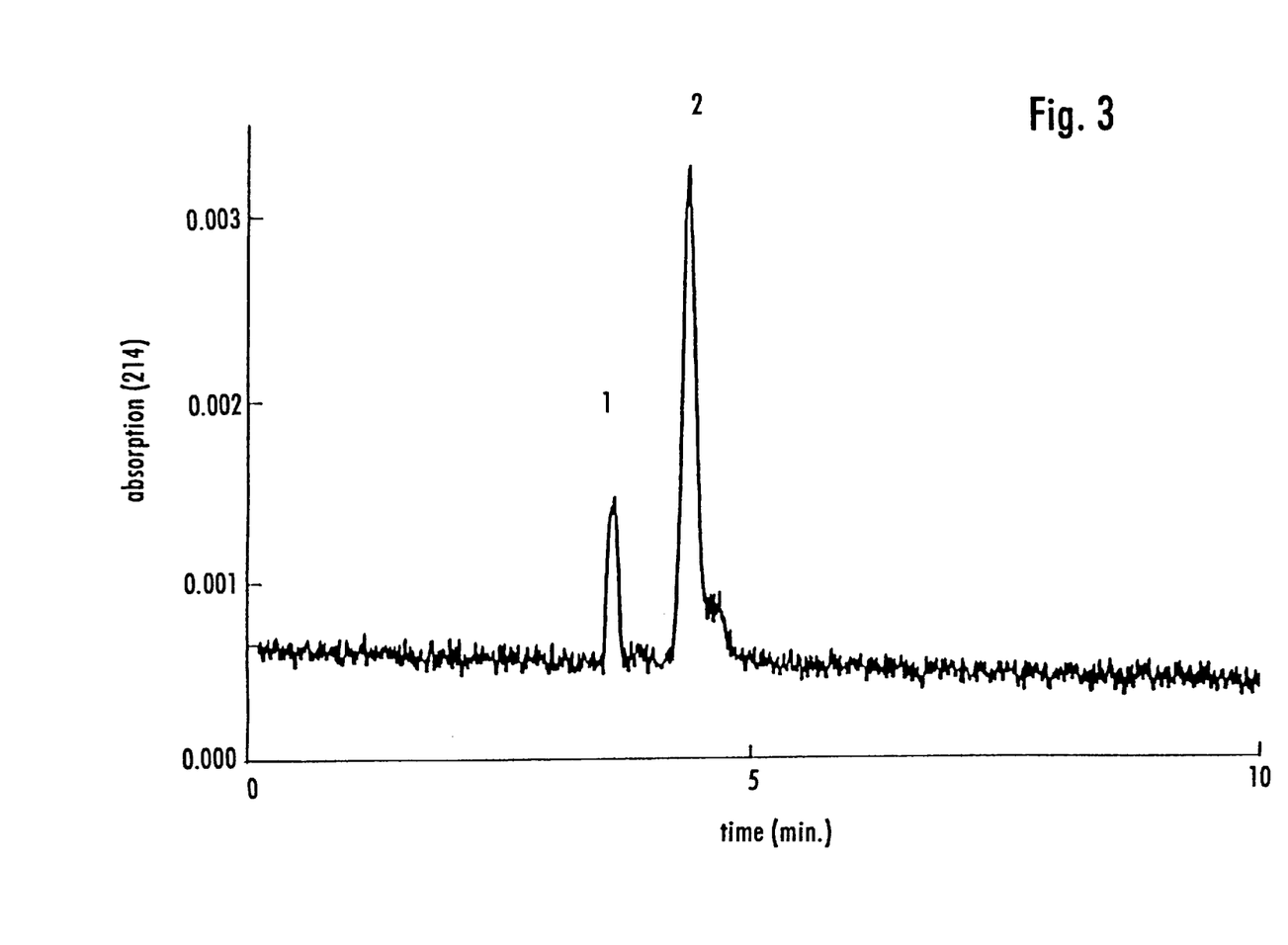
FIG. 3 is a separation of carboanhydrase in an oxidized PEEK capillary under separation conditions of L=29/35.5 cm, 50 µm ID, 100 mM TRIS/boric acid pH 8.3, carboanhydrase (2), benzyl alcohol (1).

A premanufactured untreated PEEK hollow fibre capillary is first subject to an oxidative treatment. A solution of 2.5% $KClO_3$ in $H_2SO_4/H_2O$ (1:1 v/v) is passed through the capillary at room temperature. The thus effected changes in electroosmotic flow properties are illustrated in the electropherograms as shown in the accompanying FIGS. 1, 2 and 3.

EXAMPLE 2

Figure 4:
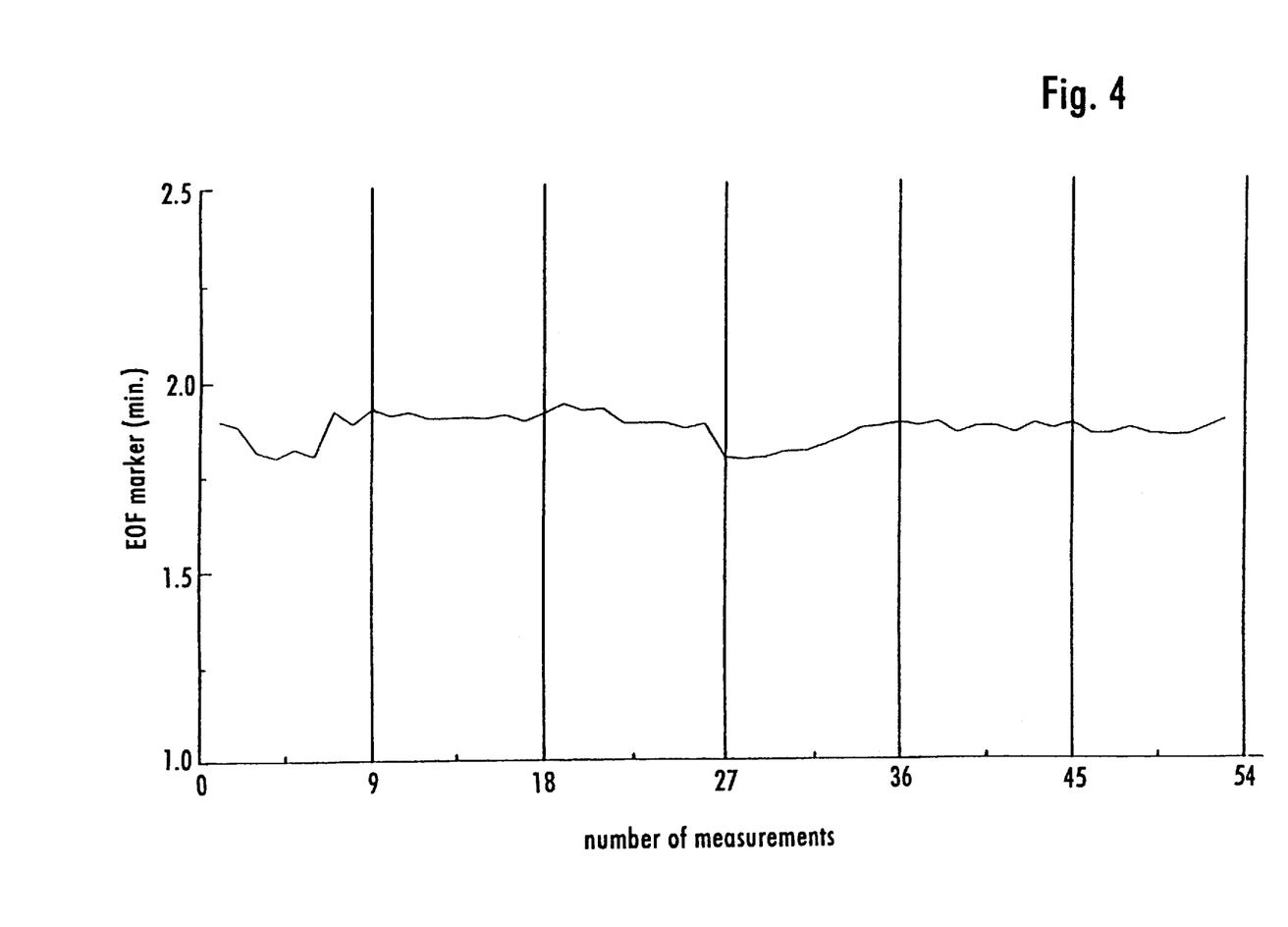
FIG. 4 is a diagram of the measurement of stability of a PEEK capillary covered with polyimine under separation conditions of L=20/27 cm, E=500 V/cm, phosphate buffer 10 mM pH 6, EOF marker: benzyl alcohol, detection window: 1.5 cm silica capillary, 50 µm ID, PEEK capillary: 50 µm ID.

A PEEK capillary pretreated by oxidation as described in Example 1 is reacted with polyethylene polyamine. The preoxidized PEEK capillary is filled with 10% polyethylene polyamine solution in methanol/water (4:1 v/v) which is subsequently sucked out and the capillary then dried at 200° c. in an air stream. At pH 6 the thus treated capillaries show an inverted EOF which remains constant over numerous measuring cycles. Results are presented in FIG. 4.

EXAMPLE 3

A PEEK capillary pretreated by oxidation as described in Example 1 is further activated by reaction with carbodiimide solution. Subsequently the carbodimide derivated PEEK capillary is reacted with an amine solution to form the corresponding amine derivative.

EXAMPLE 4

A PEEK capillary pretreated by oxidation as described in Example 1 is further reacted with $SOCl_2$, followed by an amidation reaction.

EXAMPLE 5

A PEEK capillary pretreated by oxidation as described in Example 1 is further treated with $SO_3$ vapors to effect sulfonation of the inner surface of the polymer capillary material.

EXAMPLE 6

A premanufactured untreated PTFE hollow fibre capillary is activated by a strong reductive agent in the presence of a strong base. 0.77% (w/v) benzoin solution in a 2.9% potassium tertiary butylate solution in dimethylsulfoxide are passed through the capillary at 50° C. under exclusion of air. Fluorine elimination causes unsaturated polymer chains to form on the capillary inner surface which are adapted for further derivatization.

EXAMPLE 7

Figure 5:
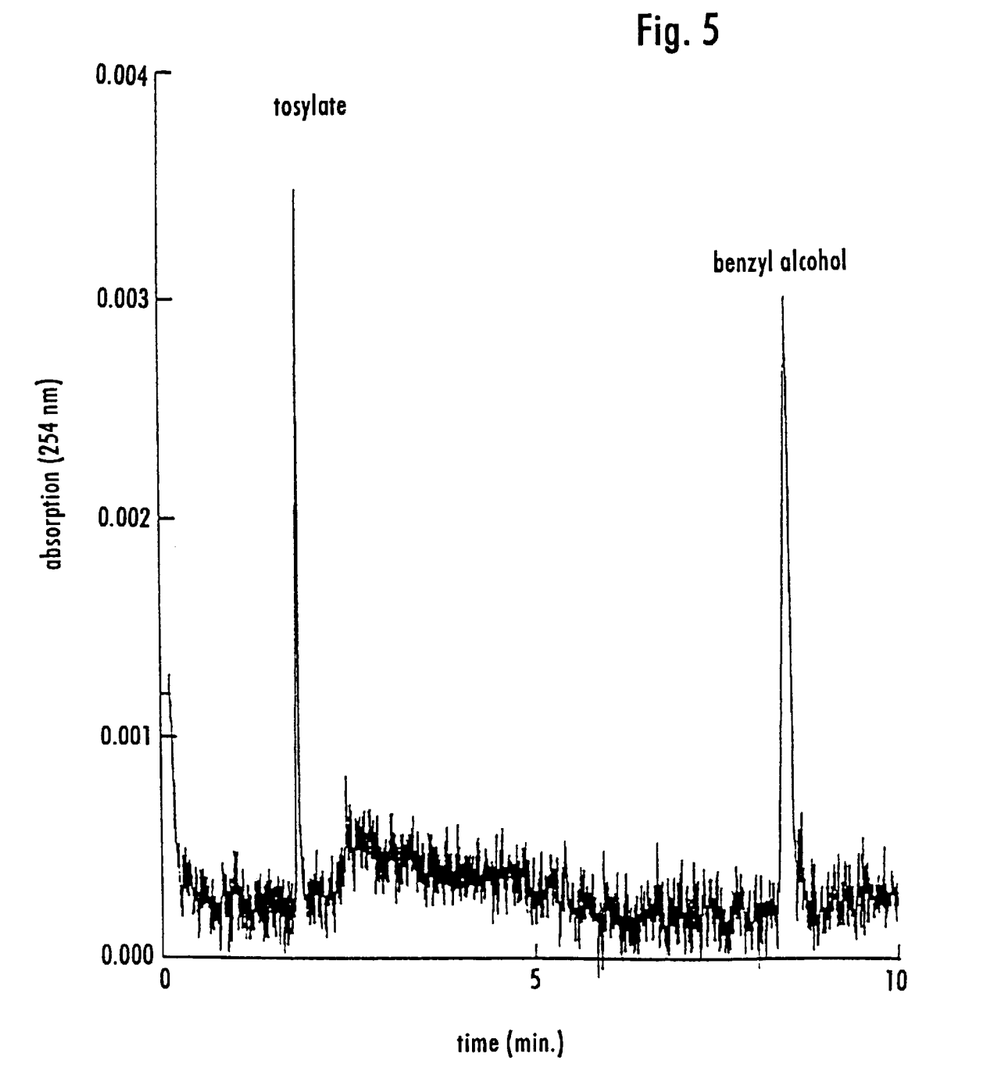
FIG. 5 is an electropherogram of tosylate and benzyl alcohol on a TEPA capillary with inversed EOF under separation conditions of L=20/27 cm, 50 µm ID, 10 mM phosphate buffer pH 3 (TEPA=tetraethylenepentamine).
Figure 6:
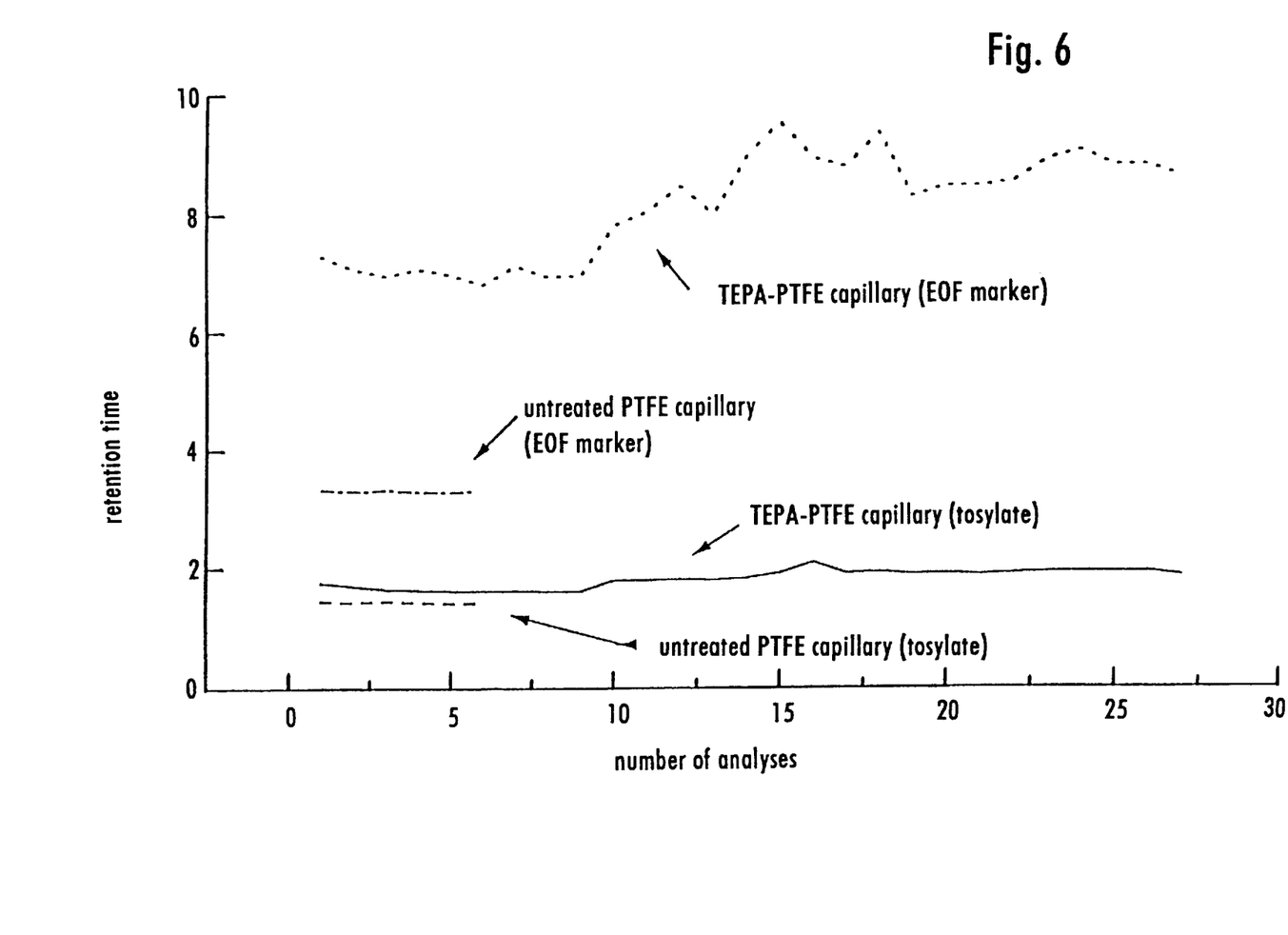
FIG. 6 is a comparison of migration times on an untreated and a TEPA-PTFE capillary under separation conditions of L=20/27 cm, 10 mM phosphate buffer pH 3.

A PTFE capillary pretreated as described in Example 6 is reacted with 0.2 molar bromine solution in $CCl_4$. Following this further activation step of Br addition, the capillary material is reacted with a 20% hexamethylene diamine solution in diethylene glycol monoethyl ether at 80° C. This produces the corresponding amine derivative of the capillary polymer material. At pH 7 the EOF is considerably decreased as compared to the EOF of the untreated PTFE capillary. At pH 3 an inversed EOF was found. Results for the anion tosylate are presented in the electropherogram as shown in FIG. 5. A comparison of migration times for the untreated and treated PTFE capillary is shown in FIG. 6.

EXAMPLE 8

A PTFE capillary pretreated as described in Example 6 is reacted with borane in tetrahydrofuran (THF) and subsequently oxidized to the alcohol derivative.

EXAMPLE 9

Figure 7:
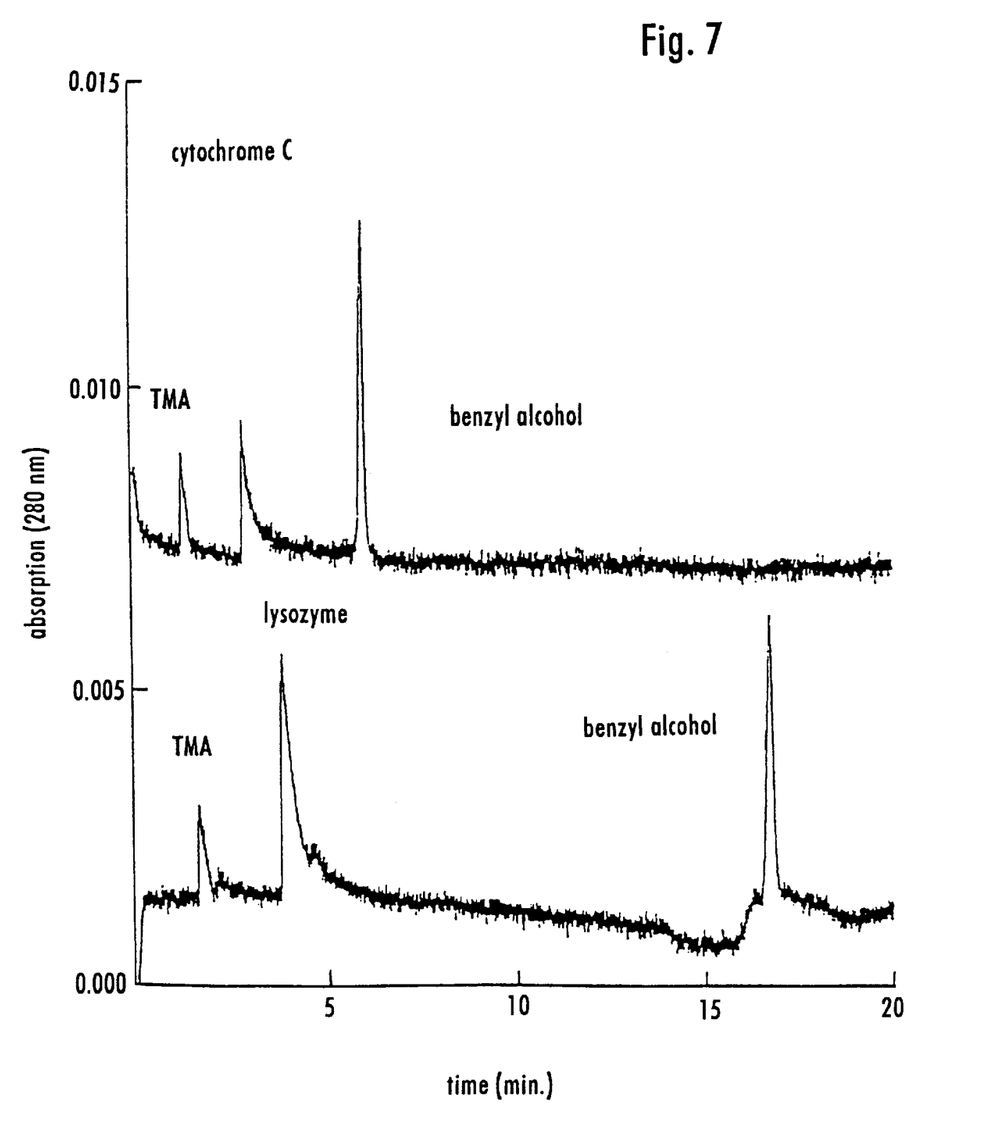
FIG. 7 is an electropherogram of lysocyme, cytochrome C, trimethylphenylammonium bromide (TMA) on an PTFE capillary activated by reaction with linear polyacrylamide under separation conditions of L=20/27 cm, 50 µm ID, 10 mM phosphate buffer pH 7, separation current 15 kV.

A PTFE capillary pretreated as described in Example 6 is reacted with ammonium persulphate and tetraethyl methylene diamine (TEMED) to introduce acrylamide to the activated polymer capillary material. The performance of the thus modified PTFE capillary in the separation of cytochrome C and lysozyme is presented in FIG. 7.

EXAMPLE 10

A PEEK capillary is reacted in a reduction step with organo lithium hydride dissolved in dry tetrahydrofuran at room temperature for up to 10 h. Subsequently the capillary is flushed first with aqueous basic and then with acidic solutions, then flushed with organic solvents like tetrahydrofuran. The capillary is subject to drying at room temperature for 25 h. Thus the original carbonyl groups of the base polymer capillary material are modified to produce OH groups showing improved hydrophilic properties.

EXAMPLE 11

A PEEK capillary is reacted in a Wittig reaction using methyltriphenyl phosphonium bromide and dimethylsulfoxide in a strong basic solution which is passed through the capillary at elevated temperature. Subsequently the capillary is flushed with dimethylsulfoxide and then with organic solvents like tetrahydrofuran. The capillary is subject to drying at room temperature. Thus the ketone groups of the polymer chains of the capillary inner surface are modified to olefin groups showing improved hydrophobic properties.

While there have been described and illustrated specific embodiments of the invention, it will be clear that variations in the details of the embodiments specifically illustrated and described may be made without departing from the true spirit and scope of the invention as defined in the appended claims.

We claim:

1. A capillary adapted for use in capillary electrophoresis comprising an original polymer material possessing an initial concentration of functional groups, wherein said capillary has an integral inner surface; wherein said integral inner surface consists essentially of the original polymer that has been chemically modified by the creation therein of additional active functional groups in a concentration that is greater than said initial concentration and is in an amount of about $3.5 \times 10^{-2}$ to $3.5 \times 10^{-1}$ $\mu M/m^2$; wherein said amount of the total active functional groups is sufficiently greater than said initial concentration of functional groups so that the inner surface of said capillary possesses properties different from the corresponding properties of the original polymer capillary material.

2. A capillary according to claim 1, wherein said inner surface has more active functional groups therein than in said original polymer capillary material.

3. A capillary according to claim 2, wherein the original polymer capillary material of said capillary is selected from the group consisting of a polyfluorocarbon and a poly etheretherketone.

4. A capillary according to claim 3, wherein said polyfluorocarbon is poly tetrafluoroethylene.

5. A capillary according to claim 2, wherein the additional functional groups on said inner surface are chemically bonded to atoms of the original polymer capillary material of said capillary.

6. A capillary according to claim 2, wherein the functional groups are predominantly hydrophilic groups.

7. A capillary according to claim 2, wherein the additional functional groups are of a kind and are present in an amount adapted to modify the electroosmotic flow (EOF) properties of said inner surface as compared to the electroosmotic flow (EOF) of said original polymer capillary material.

8. A capillary according to claim 2, wherein the additional functional groups are non-ionic.

9. A capillary according to claim 2, wherein said additional functional groups are ionic.

10. A method of separating proteins in a mixture of proteins which comprises passing said mixture through a capillary according to claim 1.

11. A capillary according to claim 1, wherein said capillary is substantially nontransparent, and further comprising an optical passage to allow optical detection.

12. A capillary according to claim 1, further including at least one optical passage through a wall of said capillary.

13. A capillary according to claim 12, wherein said optical passage comprises at least one optical lens.

14. A capillary according to claim 1, wherein the polymer material is selected from the group consisting of polyfluorocarbon and poly etheretherketone.

15. A capillary according to claim 14, wherein said polyfluorocarbon is poly tetrafluoroethylene.

16. A process for the production of a capillary adapted for use in capillary electrophoresis, wherein said capillary has an inner surface; and
wherein said capillary is made of an original polymer material having a concentration of functional groups,
wherein said process comprises:
  treating at least an inner surface of a pre-manufactured capillary with a chemical reagent which is adapted to generate functional groups directly on the capillary inner surface or is adapted to generate attachment sites in the original polymer material of said inner surface to which additional active functional groups can be bonded; and
  reacting said reagent with the original polymer material of said inner surface under conditions sufficient to generate about $3.5 \times 10^{-2}$ to $3.5 \times 10^{-1}$ $\mu M/m^2$ of active functional groups in said polymer of which said inner surface consists essentially;
  wherein the concentration of active functional groups of said reacted inner surface polymer is sufficiently greater than the concentration of functional groups in said original polymer that the properties of the treated inner surface polymer are different from the corresponding properties of said original polymer material.

17. A process according to claim 16, wherein preformed carriers of the additional active functional groups are introduced.

18. A processing according to claim 17, wherein carriers of the additional functional groups are chemically bonded to the capillary surface.

19. A process according to claim 17, wherein carriers of the additional functional groups are chemically bonded, via a linking number, to the capillary surface.

20. A process according to claim 19, wherein the carriers are chemically bonded via said linking member to the capillary surface and then said additional active functional groups are bonded to said linking number.

21. A process according to claim 20, wherein the linking member acts as a spacer.

22. A process of producing a capillary comprising:
  producing capillary tubes, having an integral inside surface, within an original polymer material;

wherein the original polymer material of the integral inside surface of said capillary tubes has a concentration of functional groups; and reacting said integral inside original polymer surface of said capillary with a chemical reagent under conditions sufficient to generate additional active functional groups on said integral inside surface of said capillary such that the concentration of active functional groups of said reacted integral inside capillary surface is about $3.5 \times 10^{-2}$ to $3.5 \times 10^{-1}$ $\mu M/m^2$; to produce an integral inside capillary surface that consists essentially of said reacted integral inside surface wherein the properties of said reacted inside capillary surface are different from the corresponding properties of said original polymer inside capillary surface.

23. A process according to claim 22, wherein the additional functional groups are generated directly from the original polymer material on the integral inside capillary surface.

24. A process according to claim 22, wherein carriers are chemically bonded via a linking member to the capillary surface, wherein the linking member is introduced first and subsequently the functional group is bonded thereon.

* * * * *